US00PP10354P

United States Patent [19]

Larsen

[11] Patent Number: Plant 10,354

[45] Date of Patent: Apr. 28, 1998

[54] OSTEOSPERMUM PLANT NAMED 'SUNNY SILVIA'

[75] Inventor: Bjarne Larsen, Odense, Denmark

[73] Assignee: Paul Ecke Ranch, Encinitas, Calif.

[21] Appl. No.: 698,339

[22] Filed: Aug. 15, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOV-ROM Plant Variety Database 'Sunny Silvia', Osteospermum, PBR OTS0017, 1994.

*Primary Examiner*—Howard J. Locker
*Assistant Examiner*—Melissa L. Kimball
*Attorney, Agent, or Firm*—Arnold, White & Durkee

[57] ABSTRACT

A new and distinct cultivar of Osteospermum named 'Sunny Silvia', particularly characterized by its upright growth habit with excellent medium purple and white bi-color flower coloration, medium flowering response time, glossy green foliage, and suitability to 6 inch pots, and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Sunny Silvia', and was developed by the inventor Bjarne Larsen in Odense, Denmark, in 1993, by crossing the cultivar designated 'Sunny Girl' with the cultivar 'Killerton Pink', an unpatented cultivar.

Asexual reproduction by terminal (stem tip) cuttings taken by me or under my supervision at Kernen Greenhouse in Odense, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. A unique flower color contrast of medium purple and white bi-color.
2. A upright compact growth habit.
3. Medium flower response.
4. Well suited for 6" pots, nursery containers, and hanging baskets.

'Sunny Silvia' is similar to the cultivar 'Sunny Girl'. The growth habit of 'Sunny Silvia' is more upright, flower petioles are shorter, and plant flower color is darker than 'Sunny Girl'.

Chart A compares 'Sunny Silvia' with 'Sunny Girl', described and illustrated in co-pending U.S. Plant Patent application Ser. No. 08/698,337 which appears to be the most closely comparable to the knowledge of the inventor.

CHART A

| Characteristic | 'Sunny Silvia' | 'Sunny Girl' |
|---|---|---|
| Plant Height (above the pot) | 32 cm | 32 cm |
| Plant Width | 48 cm | 67 cm |
| Flower Head Diameter | 9 cm | 8.8 cm |
| Flower Color - mature ray florets | RHS 78B fading to nearly white at proximal end | RHS 80C fading to RHS 155B at proximal end |

DESCRIPTION OF PHOTOGRAPH

The accompanying colored photograph is a top perspective view of the new cultivar, showing color as true as it is reasonably possible to obtain in a colored reproduction of this type.

DESCRIPTION OF THE PLANT

The following is a detailed description of my new Osteospermum cultivar based on plants grown under commercial practice in Encinitas, Calif. One rooted cutting was transplatned into a 17 cm florist pot on Jan. 8, 1996. The plant was pinched on Jan. 29, 1996, and received plant growth regulator on Feb. 12 and 26. The values, measurements and observations noted below were taken from plants in bloom on Apr. 20, 1996.

On Apr. 23, 1996, I observed a plant in a 17 cm florist pot 13 cm tall. This pot had one branched plant with an overall height of 45 cm and an overall width of 48 cm. This plant had 6 strong branches, originating from within 1.5 cm of the soil line. Each branch was approximately 33 cm long terminating in a flower. At observation, there were 9 flowers open and 85 flower buds in various stages of development. Four to five secondary shoots subtend the terminal flower from the four to five nodes on the primary shoot. These secondary shoots also terminated in a flower.

Color references are made to The Royal Horticultural Society Colour Chart (R.H.S.), except where general terms of ordinary dictionary significance are used.

THE PLANT

Origin: Seedling from cross pollination.

Parentage: Cross between Seed Parent 'Sunny Girl' and Pollen Parent 'Killerton Pink'.

Classification:

*Botanical.—Osteospermum ecklonis.*

*Common name.*—Osteospermum.

*Cultivar name.*—'Sunny Silvia'.

Asexual reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitious roots from the stem base.

D. *Growth period.*—Using standard growth retardant applications of 1–2 applications of daminozide/butanedioic acid mono (2.2 dimethylhydrazide) at a rate of 2,500 ppm. Applications are made as foliar sprays. Growth retarding chemicals generally reduce plant height by e.fra 1/3×.

Plant description:

A. *Form.*—Symmetrical, upright growing perennial shrub, with good branching characteristics after pinching, giving the plant a full appearance.

B. *Habit of growth.*—Vigorous, upright habit, producing approximately 20 leaves per stem and terminating in flowers. Flowering is continuous with shoots terminating in a flower. Additional subordinate axillary shoots arise and elongate to promote additional flowering. Plants are initially potted using rooted cuttings, pinched two weeks later, maintained at a temperature of 10°–12° C. for four weeks then grown for seven weeks at a temperature of 18° C. for a total of 13 weeks to flower.

C. *Foliage description.*—1. Leaf shape: Obovate with acuminate tip and attenuate leaf base. 2. Leaf blade size: Mature leaves 9 cm long and 3.5 cm wide. 3. Petiole length: Approximately 3.5 cm in length. 4. Leaf margin: Slightly sinuate with 3 to 6 pointed lobes on either side of the leaf blade. 5. Foliage fragrance: Characteristic osteospermum plant fragrance, particularly notable when foliage is wet. 6. Leaf texture: Slightly undulant and twisted at the tip. i) Upper surface: Slightly pubescent with short, white trichomes evenly distributed throughout the leaf surface. ii) Under surface: Glabrous. 7. Leaf color: Dark green. i) Upper surface: Near R.H.S. 147A. ii) Under surface: R.H.S. 147A-B. 8. Venation: Palmately branched with predominate light green colored mid-vein on the upper surface. One prominent mid-vein is raised on the lower surface.

Inflorescence description: Daisy type composite flower with disk and ray florets that close at night and open in the morning. The ligulate petal of the ray floret subtends the pistil. The disk florets contain male flower parts. Florets on the flower heads are imperfect with pistillate ray florets and staminate disk florets.

A. *Flowering habits.*—Flowering is determinate with one primary flower at the end of a long (19 cm) pedicel on open flowers. Each pedicel had approximately 6 leaflets on the proximal end of the pedicel. A secondary flower arises from the base of the primary pedicel.

B. *Natural flowering season.*—Flowering occurs primarily February through October in the northern hemisphere. Initiation occurs after a cool temperature vernalization (10°–17° C.). Floriferousness may wane during hot summer days in temperate climates.

C. *Flower buds.*—Flower buds develop successively on secondary branches, reaching a size of 2 cm long and 1 cm wide prior to opening.

D. *Flower borne.*—Singularly 7 cm above the plant canopy.

E. *Quantity of flowers.*—Secondary flowers occur progressively around the primary flower so that tight buds to mature flowers are visible at the same time.

F. *Flower head.*—1. Number of florets: 21 ray florets and numerous disk florets, making up a flower disk approximately 1.1 cm in diameter. 2. Shape: Narrow linear florets with obtuse to acute tipe and acute bases. Ray florets are approximately 4 cm long and 0.8 cm wide. 3. Color: Ray florets are bright bi-color medium purple to white: disk florets are violet-blue. i) Upper surface of ray florets: Near R.H.S. 78B and fading to nearly white on the sides of the florets nearer to the proximal end. ii) Under surface of ray florets: Background color light violet near R.H.S. 84D, with darker strips near the midrib, R.H.S. 84A. iii) Disk florets: Violet-blue near R.H.S. 98B. 4. Surface: i) Upper surface of ray florets: Glaborous. ii) Under surface of ray florets: Glabrous but pubescent near the base. 5. Inflorescence Size: Up to 9 cm in diameter. 6. Flower fragrance: None.

G. *Reproductive organs.*—1. Stamens: Short stamens emerge on outermost disk florets and progress toward the center. 2. Anther: Each disk floret has 1 stamen terminating in a 5-part anther. 3. Pollen: Copious and golden yellow. 4. Stigma: Bipartite. 5. Styles: Short, approximately 2 to 3 mm long and purple. 6. Ovary: Inferior to florets and green in color.

H. *Resistance.*—1. Frost: Withstands light frost. 2. Root, Stem, Foliage and Flower Diseases: Highly resistant.

What is claimed is:

1. A new and distinct cultivar of Osteospermum plant named 'Sunny Silvia' as illustrated and described.

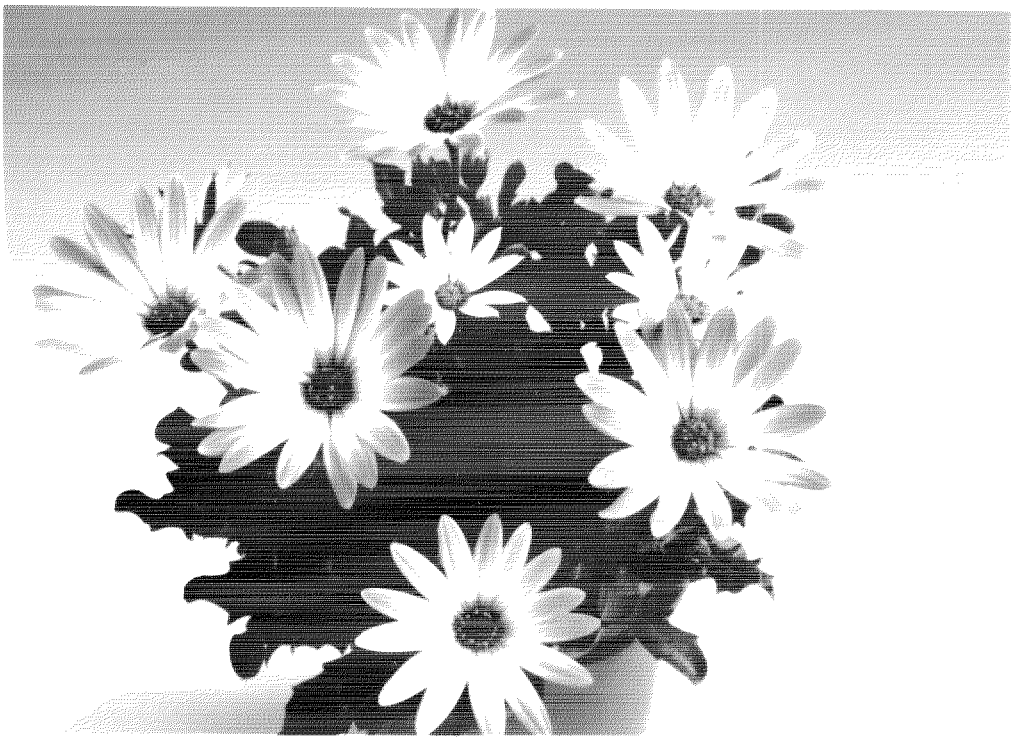

* * * * *